(12) United States Patent
Watkins et al.

(10) Patent No.: US 6,393,314 B1
(45) Date of Patent: May 21, 2002

(54) RF DRIVEN RESISTIVE ABLATION SYSTEM FOR USE IN MRI GUIDED THERAPY

(75) Inventors: Ronald Dean Watkins, Niskayuna; Kenneth William Rohling, Burnt Hills, both of NY (US); Erika Schneider, Pawcatuck, CT (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/306,083

(22) Filed: May 6, 1999

(51) Int. Cl.[7] .............................................. A61B 5/055
(52) U.S. Cl. ........................................ 600/411; 606/29
(58) Field of Search .................................. 600/411, 427; 607/96, 98, 99, 115, 101, 154–156, 122; 606/28, 29, 27, 32, 41

(56) References Cited

U.S. PATENT DOCUMENTS

| | | | |
|---|---|---|---|
| 4,431,968 A | 2/1984 | Edelstein et al. ............ 324/309 |
| 4,665,365 A | 5/1987 | Glover et al. ................ 324/309 |
| 4,719,585 A | 1/1988 | Cline et al. .................. 364/518 |
| 4,869,248 A | * 9/1989 | Narula ......................... 607/96 |
| 4,952,877 A | 8/1990 | Stormont et al. .......... 3234/312 |
| 4,992,736 A | 2/1991 | Stormont et al. ........... 324/309 |
| 5,100,388 A | * 3/1992 | Behl et al. ................... 604/113 |
| 5,122,747 A | 6/1992 | Riederer et al. ............ 324/309 |
| 5,242,441 A | * 9/1993 | Avitall .......................... 606/41 |
| 5,263,493 A | * 11/1993 | Avitall ......................... 607/122 |
| 5,271,400 A | 12/1993 | Dumoulin et al. ........ 128/653.2 |
| 5,307,808 A | 5/1994 | Dumoulin et al. ........ 128/653.2 |
| 5,318,025 A | 6/1994 | Dumoulin et al. ........ 128/653.2 |
| 5,353,795 A | 10/1994 | Souza et al. .............. 128/653.2 |
| 5,433,708 A | * 7/1995 | Nichols et al. ............. 604/113 |
| 5,437,277 A | 8/1995 | Dumoulin et al. ........ 128/653.1 |
| 5,568,384 A | 10/1996 | Robb et al. ............. 364/419.13 |
| 5,617,857 A | 4/1997 | Chader et al. ............ 128/653.1 |
| 5,622,170 A | 4/1997 | Schulz ..................... 128/653.1 |
| 5,674,191 A | * 10/1997 | Edwards et al. .............. 604/22 |
| 5,715,822 A | 2/1998 | Watkins et al. .......... 128/653.5 |
| 5,762,065 A | 6/1998 | Prince ..................... 128/653.4 |
| 5,935,123 A | * 8/1999 | Edwards et al. .............. 606/41 |
| 6,012,457 A | * 1/2000 | Lesh .......................... 607/122 |
| 6,016,439 A | * 1/2000 | Acker ........................ 600/411 |
| 6,045,532 A | * 4/2000 | Eggers et al. ................ 604/114 |
| 6,047,218 A | * 4/2000 | Whayne et al. ............. 607/122 |
| 6,091,995 A | * 7/2000 | Ingle et al. .................. 607/138 |

* cited by examiner

Primary Examiner—Ruth S. Smith
(74) Attorney, Agent, or Firm—Jean K. Testa; Donald S. Ingraham

(57) ABSTRACT

An MRI system acquires NMR image data to produce real time anatomic images as an ablation device is guided into contact with target tissues in a patient to be thermally treated. The ablation device includes a resistive element at its operating end which receives alternating current from an ablation control system. The resistive element produces therapeutic heat that treats the target tissues.

10 Claims, 3 Drawing Sheets

RF DRIVEN RESISTIVE ABLATION SYSTEM FOR USE IN MRI GUIDED THERAPY

BACKGROUND OF THE INVENTION

The field of this invention is nuclear magnetic resonance imaging (MRI) methods and systems. More particularly, the invention relates to ablation devices for use during MRI guided thermal therapy.

Thermal energy deposition is often used in medicine as a means of necrosing diseased tissue. Lasers, radio frequency antennas and ultrasonic transducers are examples of devices used for the deposition of thermal energy for therapy. It is desirable to have a means of guiding and monitoring this energy deposition to assure the energy is applied in the proper location and to verify that appropriate energy levels are used to prevent undertreatment or overtreatment. Magnetic resonance imaging has been demonstrated as a method for identifying regions of tissue to be treated, guiding therapeutic- devices and biopsy needles as well as monitoring the deposition of thermal energy from lasers, ultrasound devices or cryogenic probes.

Intra-operative MR imaging is employed during a medical procedure to assist the physician in guiding an instrument. For example, during ablation therapy the MRI system is operated in a real-time mode in which image frames are produced at a high rate so that the location of the ablation device can be monitored as it is inserted. A locator device, such as that described, for example, in Dumoulin et al. U.S. pat. No. 5,271,400 issued Dec. 21, 1993 or Dumoulin et al. U.S. pat. No. 5,307,808, both of which are assigned-to the instant assignee, may be used to track the location of the instrument and provide coordinate values to the MRI system which enable it to mark the location of the instrument in each reconstructed image. The medical instrument is attached to a handpiece that is manipulated by the physician and whose position is detected by surrounding sensors. For example, the handpiece may emit light from two or more light emitting diodes that is sensed by three stationary cameras.

Systems which employ the MRI system to locate markers in the medical device have also been developed. Such tracking systems employ a small coil attached to a catheter or other medical device to be tracked. An MR pulse sequence is performed using the tracking coil to acquire a signal that indicates location of the tracked device. The location of the tracking coil is determined and is superimposed at the corresponding location in a medical image acquired with the same MRI system.

Other techniques to perform ablation therapy also exist. Some of these techniques cannot be used in the high magnetic field and low noise environment of an MRI system. Any device used in the bore of the magnet can distort the precise magnetic and radio frequency fields required for accurate imaging. In addition, the current carried by electrical devices produces a local magnetic field that produces artifacts in the acquired images.

SUMMARY OF THE INVENTION

An ablation system which employs a resistive device is guided into position using MRI and is then energized with electric power to treat target tissues. The system includes an ablation device that contains a resistive element, an MRI system which acquires image data from a patient undergoing treatment with the ablation device, and an ablation control for providing alternating current to the resistive element to produce heat for treating target tissues. The frequency of the current is set to a value such that the alternating current does not produce artifacts in the images reconstructed from the acquired image data.

DESCRIPTION OF THE PREFERRED EMBODIMENT

Figure 1:
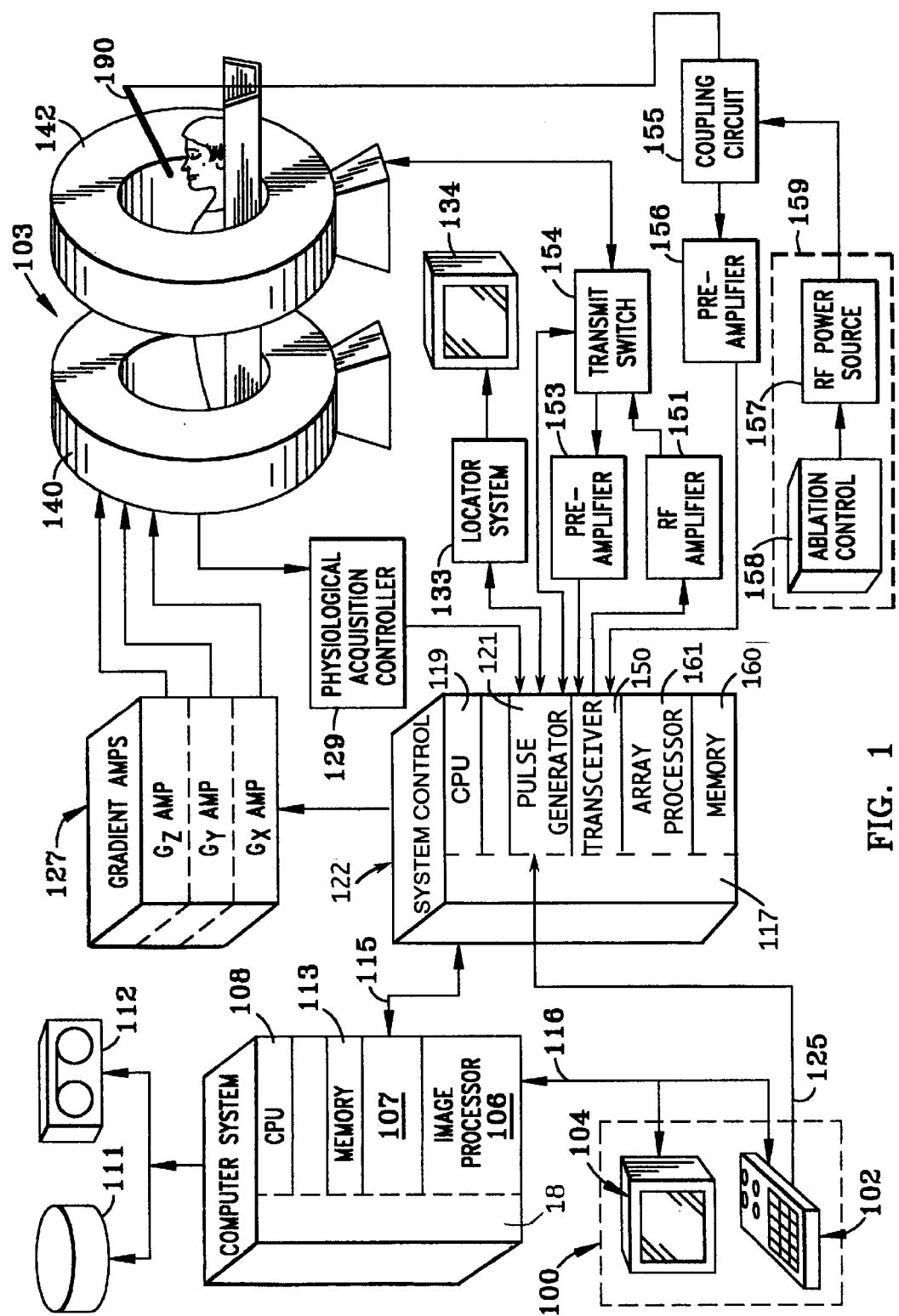
FIG. 1 is a block diagram of an MRI system employing the present invention.

FIG. 1 illustrates the major components of an MRI system that incorporates the invention. Operation of the system is controlled from an operator console 100 which includes a keyboard and control panel 102 and a display 104. Console 100 communicates through a link 116 with a separate computer system 107 that enables an operator to control the production and display of images on a screen of display 104. Computer system 107 includes a number of modules which communicate with each other through a backplane 118. These include an image processor module 106, a CPU (central processing unit) module 108, and a memory module 113 which is known in the art as a frame buffer for storing image data arrays. Computer system 107 is linked to a disk storage 111 and a tape drive 112 for storage of image data and programs, and communicates with a separate system control 122 through a high speed serial link 115.

System control 122 includes a set of modules coupled together by a backplane 117. These include a CPU module 119 and a pulse generator module 121 which is coupled to operator console 100 through a serial link 125. System control 122 receives commands from the system operator through link 125 which indicate the scan sequence to be performed. Pulse generator module 121 operates the system components to carry out the desired scan sequence, producing data that indicate the timing, strength and shape of the RF pulses to be produced, and the timing of and length of the data acquisition window. Pulse generator module 121 is coupled to a set of gradient amplifiers 127 to control the timing and shape of the gradient pulses to be produced during the scan. Pulse generator module 121 also receives. patient data from a physiological acquisition controller 129 that receives signals from sensors attached to the patient, such as ECG (electrocardiogram) signals from electrodes or respiratory signals from a bellows.

The gradient waveforms produced by pulse generator module 121 are applied to gradient amplifier system 127 comprised of $G_x$, $G_y$, and $G_z$ amplifiers. Each gradient amplifier excites a corresponding gradient coil in the magnet system 103 to produce the magnetic field gradients used for position encoding acquired signals. Pulse generator module 121 also produces an output signal for an ablation control 158 to coordinate the ablation process with the image acquisition process.

A transceiver module 150 in system control 122 produces pulses which are amplified by an RF (radio frequency)

amplifier 151 and supplied to an RF coil in magnet assembly 103 by a transmit/receive switch 154. The resulting signals radiated by the excited nuclei in the patient may be sensed by the same RF coil and supplied through the transmit/receive switch 154 to a preamplifier 153. The amplified NMR (nuclear magnetic resonance) signals are demodulated, filtered, and digitized in the receiver section (not shown) of transceiver 150. Transmit/receive switch 154 is controlled by a signal from pulse generator module 121 to electrically connect the RF coil to RF amplifier 151 during the transmit mode and to preamplifier 153 during the receive mode.

The NMR signals acquired by an RF coil are digitized by transceiver module 150 and transferred to a memory module 160 in system control 122. When an array of k-space (i.e., spatial frequency space) image data has been acquired in memory module 160, an array processor 161 operates to Fourier transform the k-space data into an array of image data which is presented to the attending physician on a display 134. The image data may also be conveyed through serial link 115 to computer system 107 where it is stored in disk memory 111. In response to commands received from operator console 100, the image data may be archived on tape drive 112, or may be further processed by image processor 106 and conveyed to operator console 100 and presented on display 104.

The system of FIG. 1 includes an ablation device 190 that is guided into a position in which a patient located in the bore of magnet system 103 may be treated. A preferred ablation device 190 includes an RF tracking coil (not shown) that serves the purpose of acquiring NMR tracking data. Tracking coil measurement acquisitions, such as those described in S. P. Souza et al. U.S. Pat. No. 5,353,795, issued Oct. 11, 1994 and assigned to the instant assignee, may be interleaved with the acquisition of image data. NMR signals from the tracking coil are supplied through a coupling circuit 155 to a second preamplifier 156. The acquired NMR tracking data are Fourier transformed by array processor 161 and used by a locator system 133 to produce an icon, representing the ablation device, for presentation on display 134. The icon is overlaid on the NMR image of the patient anatomy at the location indicated by the tracking coil.

While a conventional MRI system may be used to implement the invention, in the preferred embodiment an MRI system designed to allow access by a physician is employed. When an intra-operative MR imaging procedure is conducted, a patient is placed in magnet system 103 and a region of interest in the patient is aligned near the system isocenter located between the two, spaced magnet rings 140 and 142. A physician standing between magnet rings 140 and 142 has good access to the region of interest in the patient.

Figure 2:
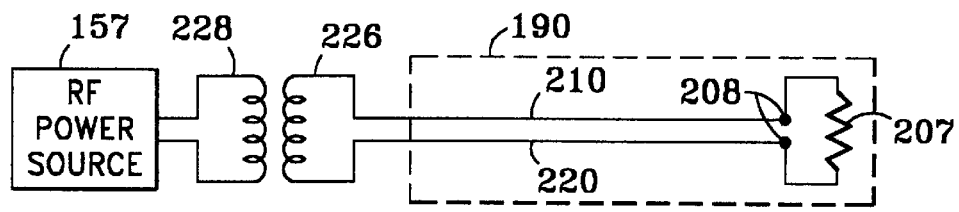
FIG. 2 is a schematic diagram of a preferred embodiment of an ablation device used with the MRI system of FIG. 1.
Figure 3:
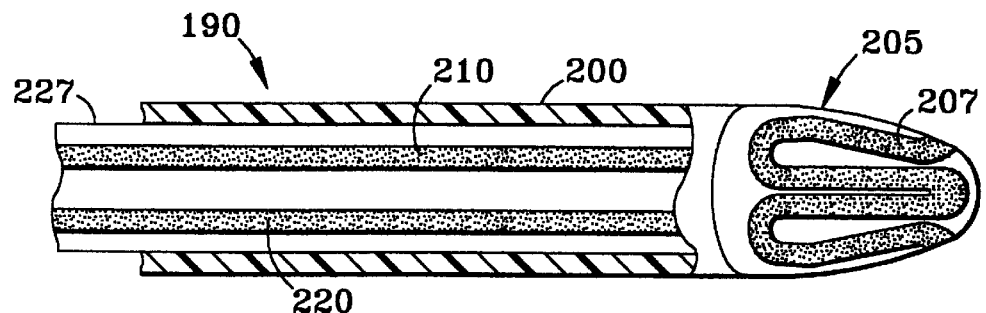
FIG. 3 is a partial pictorial view of the ablation device of FIG. 2.

FIGS. 2 and 3 show the preferred ablation device 190 as a catheter having a flexible tubular body 200 which is suitable for insertion into a patient. The diameter and length of body 200 depends on the particular medical procedure being performed, but for cardiac ablation for example, body 200 may have a length of 135 cm and a diameter of 1 mm. Body 200 is formed of a material which provides the necessary strength and flexibility and which has a magnetic susceptibility matching that of human tissue. The latter characteristic is important when used in an MRI system so that image artifacts are not produced due to perturbation of the main polarizing magnetic field $B_o$. Tubular body 200 is also a non-conductive electrical insulator.

At the operating (distal) end of ablation device 190 is a treatment tip 205 attached to the end of tubular body 200. The treatment tip 205 is rounded and is constructed of a ceramic material which is non-conductive and heat resistant, and which has a magnetic susceptibility similar to that of human tissue. A serpentine resistance element 207 is formed on ceramic tip 205 using a resistive ink which is then dried and protected with a non-conductive coating. The length of resistance element 207 is sufficient to generate the heat needed for ablation, and the path of element 207 is shaped to minimize any loops that might produce disturbing magnetic fields. For example, a bifilar winding path can be used in which the second half of the winding path is closely adjacent the first half of the winding path and matches the first half of the winding path in impedance, but conducts current in the opposite direction. The fields produced by the two halves of the winding path thus substantially cancel.

Resistance element 207 terminates in a pair of terminals 208 which connect to respective electrical conductors 210 and 220. Conductors 210 and 220 extend through the entire length of tubular body 200 and connect to a coil 226 at the proximal end of ablation device 190. Conductors 210 and 220 have very low electrical resistance and are formed by depositing a metal film on a flexible substrate 227. No ferromagnetic materials are used that might disturb the imaging fields produced by the MRI system.

An alternative device to the intravasculature device described above may have a more rigid tubular body. Such a "needle" device is more suitable for laparoscopic image-guided ablation of specific organs such as the liver, kidneys, brain, prostate or breast.

Figure 4:
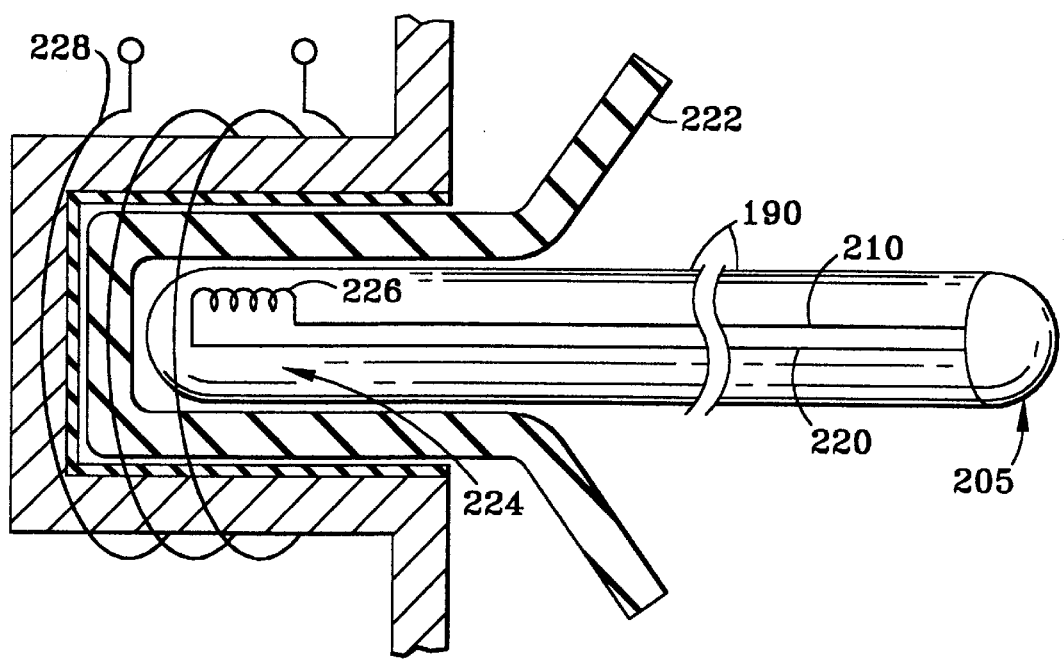
FIG. 4 is a partial schematic diagram of a coupling circuit for coupling the ablation device of FIGS. 2 and 3 to an RF (radio frequency) power source.

Coupling circuit 155 (FIG. 1) used to connect an RF power source 157 (FIG. 1) to ablation device 190 can take any one of a number of forms. In one embodiment, shown in FIG. 4, a series capacitor 230 and a parallel inductor 231 form an impedance matching circuit that couples the output of RF power source 157 (FIG. 1) to conductors 210 and 220. In another embodiment, a length of transmission line is used to perform this impedance matching function. In the preferred embodiment however, electrical isolation and impedance matching is provided by a transformer circuit, shown in FIG. 4.

Figure 5:
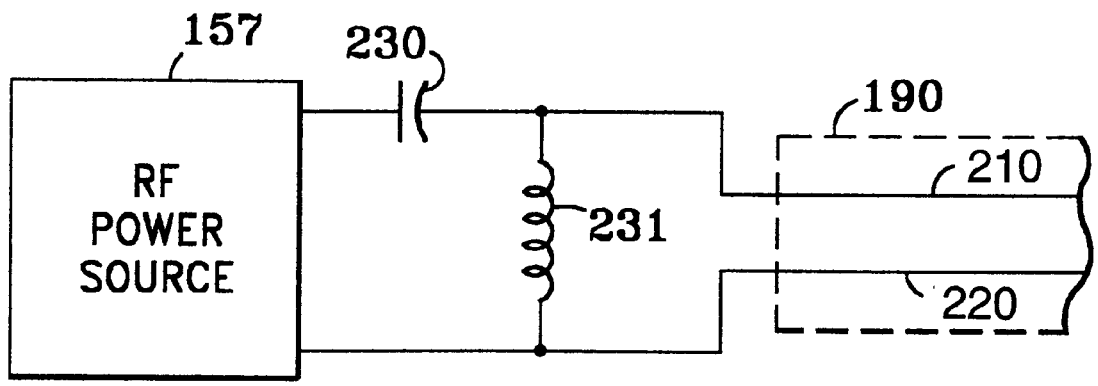
FIG. 5 is a schematic view of a transformer system for coupling the ablation device of FIGS. 2 and 3 to an RF power source.

FIG. 5 illustrates inductive coupling used to connect RF power source 157 (FIG. 2) to ablative device 190. Inductive coupling of ablative device 190 can be implemented as described in U.S. Pat. No. 5,437,277 which is incorporated herein by reference. A sterile barrier 222 is placed between the RF power source 157 and the non-operating (proximal) end 224 of ablative device 190. Conductors 210 and 220 are terminated in coil 226 which is inductively coupled to a surrounding coil 228 on the other side of the sterile barrier 222. Coil 228 is coupled to the RF power source 157 (FIG. 2) and matches its output impedance.

The RF power source 157 (FIG. 1) forms part of an ablation control system 159 with ablation control 158 (FIG. 1) which produces a measured amount of current to resistive element 207 in the operating tip of ablation device 190. This alternating current produces heat equal to the $I^2R$ power dissipated by resistance element 207, and it is this heat which raises the temperature of surrounding tissues and performs the ablative therapy. A sensor (not shown) may also be mounted in ceramic tip 205 and connected by separate conductors to provide temperature feedback signals to ablation control system 159 to enable more precise ablation temperatures to be produced.

Although resistance element 207 is inherently a direct current device, use of direct current to produce resistive heating creates magnetic fields which cause artifacts in the MR images. This problem is solved by using an alternating current at a frequency above that used to switch the magnetic field gradients and well below the Larmor frequency of the MRI system. As a result, the local induced magnetic field is averaged to zero during the MR acquisition. In the preferred embodiment a frequency of 1 to 5 MHz is employed.

While only certain preferred features of the invention have been illustrated and described, many modifications and changes will occur to those skilled in the art. For example, the invention may be employed in a wide variety of ablation devices that are inserted into a patient and brought into thermal contact with tissues to be ablated. Also, control of the ablation process can be performed in many ways, ranging from manual control by the physician to totally automatic control using time and temperature feedback signals. It is, therefore, to be understood that the appended claims are intended to cover all such modifications and changes as fall within the true spirit of the invention.

What is claimed is:

1. An ablation system comprising:

an ablation device having an operating tip for guidance by a physician into a treatment position adjacent target tissues in a patient;

a resistive element mounted in the ablation device near said operating tip;

conductors positioned in the ablation device and connected to the resistive element, said conductors extending from the operating tip toward a non-operating end of the ablation device;

a MRI system for acquiring image data from the patient being treated and being operable to display an image reconstructed from the acquired image data which depicts location of the operating tip of the ablation device in the patient; and an ablation control system including a power source coupled to the conductors to deliver alternating current to the resistive element for treating the target tissues, the alternating current being above a predetermined frequency at which gradient coils of the MRI system are switched and being below the Larmor frequency of the MRI system.

2. The ablation system as recited in claim 1 in which the power source is inductively coupled to the conductors.

3. The ablation system as recited in claim 2 including a first coil disposed at the non-operating end of the ablation device and a second coil coupled to said power source, said second coil being inductively coupled to the first coil.

4. The ablation system as recited in claim 1 in which the resistive element is formed by depositing a resistive material on the operating tip.

5. The ablation system as recited in claim 4 in which the operating tip comprises a ceramic material.

6. The ablation system as recited in claim 1 in which the ablation device comprises a catheter having a flexible body.

7. The ablation system as recited in claim 1 in which the ablation device comprises a needle having a rigid body.

8. The ablation system as recited in claim 1 including a coupling circuit for coupling the conductors to the power source, said coupling circuit being operable to impedance match the power source to the conductors.

9. The ablation system as recited in claim 8 in which the coupling circuit includes a transformer.

10. The ablation system as recited in claim 8 in which the coupling circuit includes an inductor and a capacitor.

* * * * *